United States Patent
Copa et al.

(10) Patent No.: US 7,771,443 B2
(45) Date of Patent: Aug. 10, 2010

(54) ANASTOMOSIS DEVICE APPROXIMATING STRUCTURE CONFIGURATIONS

(75) Inventors: Vincent G. Copa, Minnetonka, MN (US); Kory P. Hamel, Bloomington, MN (US); Suranjan Roychowdhury, Plymouth, MN (US); Robert L. Rykhus, Edina, MN (US)

(73) Assignee: AMS Research Corporation, Minnetonka, MN (US)

( * ) Notice: Subject to any disclaimer, the term of this patent is extended or adjusted under 35 U.S.C. 154(b) by 777 days.

(21) Appl. No.: 11/437,960

(22) Filed: May 19, 2006

(65) Prior Publication Data

US 2006/0264985 A1    Nov. 23, 2006

Related U.S. Application Data

(60) Provisional application No. 60/682,944, filed on May 20, 2005.

(51) Int. Cl.
*A61B 17/08* (2006.01)
(52) U.S. Cl. .................................... 606/153
(58) Field of Classification Search ................. 606/153
See application file for complete search history.

(56) References Cited

U.S. PATENT DOCUMENTS

| | | | |
|---|---|---|---|
| 4,368,736 A * | 1/1983 | Kaster | 606/153 |
| 4,701,162 A | 10/1987 | Rosenberg | |
| 4,705,502 A * | 11/1987 | Patel | 604/544 |
| 4,792,330 A | 12/1988 | Lazarus et al. | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |

(Continued)

FOREIGN PATENT DOCUMENTS

WO    WO 92/04869    4/1992

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner*—(Jackie) Tan-Uyen T Ho
*Assistant Examiner*—Son Dang
(74) *Attorney, Agent, or Firm*—Jose' W. Jimenez; Kimberly K. Baxter; Gregory L. Koeller

(57) ABSTRACT

A surgical tool including an elongated body having a proximal end and a distal end, first and second sets of tissue approximating structures having deployed and retracted positions relative to the elongated body, an actuating mechanism at the proximal end of the elongated body for independently deploying and retracting each of the first and second sets of tissue approximating structures, and a drainage lumen extending from a drainage aperture at the distal end of the elongated body to the proximal end. The tool further includes a main balloon adjacent to the distal end of the elongated body, wherein the first set of tissue approximating structures has a different configuration than the second set of tissue approximating structures.

23 Claims, 9 Drawing Sheets

U.S. PATENT DOCUMENTS

| | | | |
|---|---|---|---|
| 4,932,956 A | | 6/1990 | Reddy et al. |
| 4,932,958 A | * | 6/1990 | Reddy et al. .................. 606/192 |
| 4,946,449 A | * | 8/1990 | Davis, Jr. ..................... 604/256 |
| 5,047,039 A | | 9/1991 | Avant et al. |
| 5,071,429 A | * | 12/1991 | Pinchuk et al. .............. 606/192 |
| 5,112,306 A | * | 5/1992 | Burton et al. ........... 604/101.02 |
| 5,123,908 A | | 6/1992 | Chen |
| 5,152,772 A | | 10/1992 | Sewell, Jr. |
| 5,306,226 A | * | 4/1994 | Salama ......................... 600/29 |
| 5,322,501 A | * | 6/1994 | Mahmud-Durrani ........... 604/8 |
| 5,540,701 A | | 7/1996 | Sharkey et al. |
| 5,545,171 A | | 8/1996 | Sharkey et al. |
| 5,695,504 A | * | 12/1997 | Gifford et al. ................ 606/153 |
| 5,707,380 A | | 1/1998 | Hinchliffe et al. |
| 5,833,698 A | | 11/1998 | Hinchliffe et al. |
| 5,836,967 A | * | 11/1998 | Schneider ................... 606/198 |
| 5,931,842 A | | 8/1999 | Goldsteen et al. |
| 5,951,576 A | * | 9/1999 | Wakabayashi ............... 606/151 |
| 5,964,791 A | | 10/1999 | Bolmsjo |
| 6,024,748 A | | 2/2000 | Manzo et al. |
| 6,119,045 A | | 9/2000 | Bolmsjo |
| 6,149,667 A | | 11/2000 | Hovland et al. |
| 6,193,734 B1 | | 2/2001 | Bolduc et al. |
| 6,238,368 B1 | | 5/2001 | Devonec |
| 6,254,570 B1 | * | 7/2001 | Rutner et al. ........... 604/101.02 |
| 6,280,460 B1 | * | 8/2001 | Bolduc et al. ................ 606/222 |
| 6,299,598 B1 | | 10/2001 | Bander |
| 6,302,905 B1 | | 10/2001 | Goldsteen et al. |
| 6,391,039 B1 | | 5/2002 | Nicholas et al. |
| 6,416,545 B1 | | 7/2002 | Mikus et al. |
| 6,440,146 B2 | | 8/2002 | Nicholas et al. |
| 6,447,533 B1 | | 9/2002 | Adams |
| 6,461,367 B1 | * | 10/2002 | Kirsch et al. ................. 606/144 |
| 6,485,496 B1 | | 11/2002 | Suyker et al. |
| 6,494,908 B1 | | 12/2002 | Huxel et al. |
| 6,520,974 B2 | | 2/2003 | Tanner et al. |
| 6,530,932 B1 | | 3/2003 | Swayze et al. |
| 6,562,024 B2 | | 5/2003 | Alvarez de Toledo et al. |
| 6,565,579 B2 | | 5/2003 | Kirsch et al. |
| 6,602,243 B2 | | 8/2003 | Noda |
| 6,695,787 B2 | * | 2/2004 | Hogendijk et al. .......... 600/463 |
| 6,695,832 B2 | | 2/2004 | Schon et al. |
| 6,702,825 B2 | | 3/2004 | Frazier et al. |
| 6,719,709 B2 | * | 4/2004 | Whalen et al. ............... 600/587 |
| 6,719,749 B1 | | 4/2004 | Schweikert et al. |
| 6,726,697 B2 | | 4/2004 | Nicholas et al. |
| 6,740,098 B2 | | 5/2004 | Abrams et al. |
| 6,746,456 B2 | | 6/2004 | Xiao |
| 6,746,472 B2 | | 6/2004 | Frazier et al. |
| 2001/0049492 A1 | | 12/2001 | Frazier et al. |
| 2002/0002363 A1 | | 1/2002 | Urakawa et al. |
| 2002/0087176 A1 | | 7/2002 | Greenhalgh |
| 2003/0069629 A1 | | 4/2003 | Jadhav et al. |
| 2003/0208183 A1 | | 11/2003 | Whalen et al. |
| 2003/0229364 A1 | | 12/2003 | Seiba |
| 2004/0078047 A1 | | 4/2004 | Nicholas et al. |
| 2004/0087995 A1 | * | 5/2004 | Copa et al. ................... 606/192 |
| 2005/0070938 A1 | * | 3/2005 | Copa et al. ................... 606/153 |
| 2005/0131431 A1 | | 6/2005 | Copa et al. |
| 2005/0251155 A1 | * | 11/2005 | Orban ......................... 606/153 |
| 2006/0200177 A1 | * | 9/2006 | Manzo ........................ 606/153 |

FOREIGN PATENT DOCUMENTS

| | | |
|---|---|---|
| WO | WO 96/07447 | 3/1996 |
| WO | WO99/16359 | 4/1999 |
| WO | WO 99/21490 | 5/1999 |
| WO | WO 99/21491 | 5/1999 |
| WO | WO 99/58081 | 11/1999 |
| WO | WO 04/000135 | 12/2003 |
| WO | WO 04/000136 | 12/2003 |
| WO | WO 04/000137 | 12/2003 |
| WO | WO 04/000138 | 12/2003 |
| WO | WO 2004/034913 | 4/2004 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

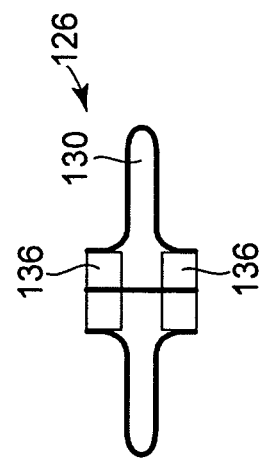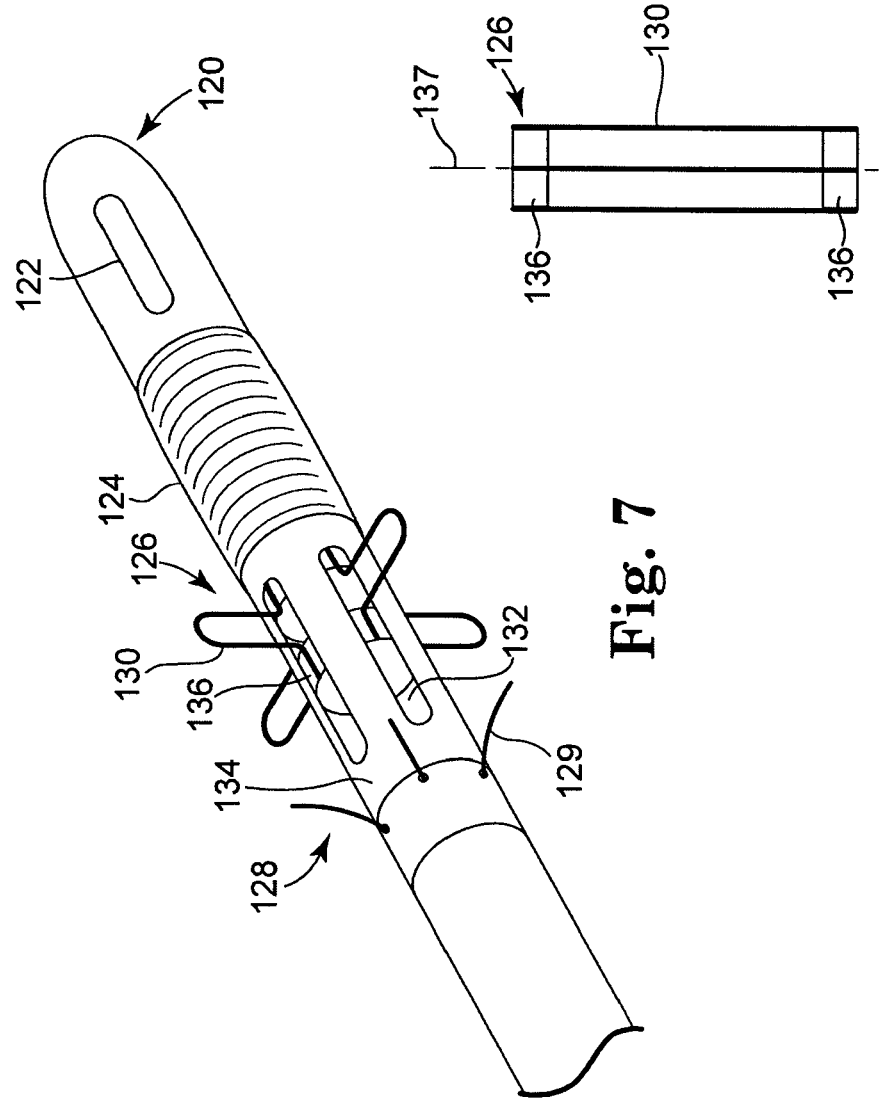

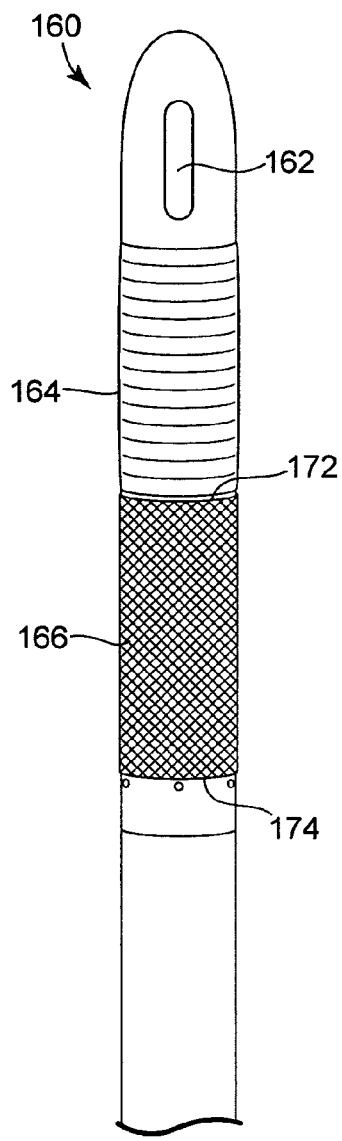
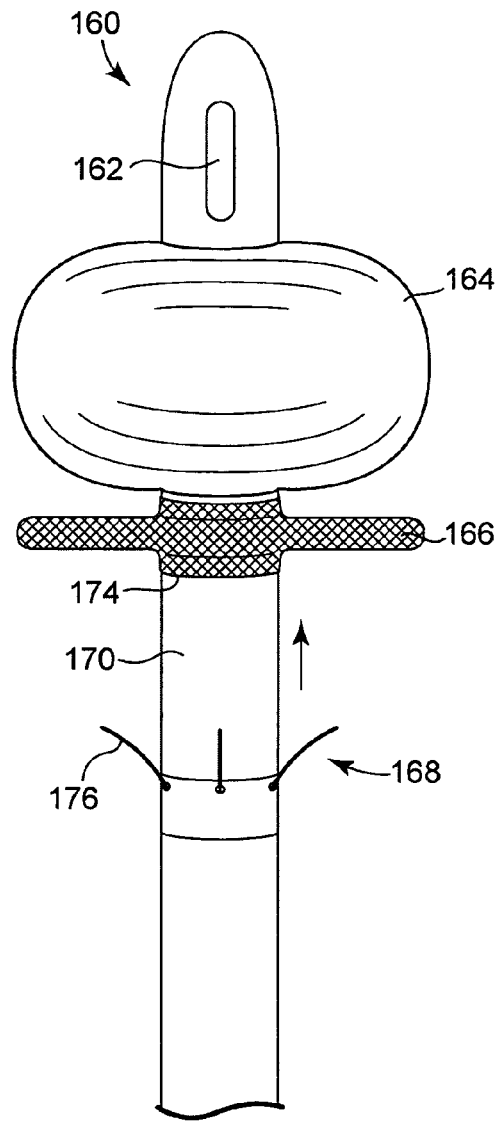
Fig. 11  Fig. 12

ANASTOMOSIS DEVICE APPROXIMATING STRUCTURE CONFIGURATIONS

CROSS REFERENCE TO RELATED APPLICATIONS

This application claims priority to U.S. Provisional application having Ser. No. 60/682,944, filed May 20, 2005, entitled "ANASTOMOSIS DEVICE CONFIGURATIONS", which application is incorporated herein by reference in its entirety.

TECHNICAL FIELD

The present invention relates to devices used for performing anastomosis and other related surgical procedures, including urethral procedures that involve reconnecting urethra and bladder tissues after a radical prostatectomy, vesicourethral anastomosis, and end-to-end urethral anastomosis.

BACKGROUND OF THE INVENTION

Anastomosis procedures are required for connecting or re-connecting certain body tissues, such as in performing part of a surgical procedure. In particular, anastomosis procedures are used for joining one hollow vessel or structure to another hollow vessel or structure so that the interior portions of the vessel can communicate with each other. In one type of procedure, which may be referred to as an end-to-end anastomosis, severed tissues of a first vessel are coupled, usually by suturing or stapling, to severed tissues of a second vessel. The tissues may be part of a body lumen such as a blood vessel, intestinal or other digestive system tissue, or tissues relating to the urinary system. As one example, in a radical prostatectomy, a surgeon removes all or most of a patient's prostate. Because the urethra travels through the prostate immediately before reaching the bladder, the upper part of the urethra is also removed with the surgery. The procedure leaves a severed urethral stump and a severed bladder neck. To restore proper urinary functions, the bladder and the urethra must be reconnected, which can be a relatively difficult and complex procedure. These difficulties can occur as a result of the tendency of the urethral stump to retract into adjacent tissue after being severed and also due to the fact that the urethral stump is obscured by the pubic bone. These and other factors can make the area difficult to access by the surgeon, particularly for extended periods of time when performing the surgical procedure.

Conventionally, a surgeon may execute delicate suturing operations with tiny, fine needles to reconnect these or other anatomical bodies. However, installation of sutures with a needle to connect severed tissues within the body of a patient can be a difficult and technique-sensitive task. Many factors can make the task difficult, including a very small amount of tissue to work with (e.g., at the urethral stump and at the bladder neck), and proximal sensitive tissues such as ureters at a bladder and a proximal nerve bundle and sphincter at a urethral stump. These factors result in complicated and delicate suturing procedures that, if not performed properly, could result in complications such as leakage, difficulty in healing or failure to heal, or specific conditions such as incontinence or impotence.

To reduce the risks involved in conventional suturing procedures, anastomosis devices have been developed that include a drainage feature and tissue approximating structures that allow for reconnection of tissues without using traditional sutures. These anastomosis devices advantageously use tissue approximating structures to reconnect severed tissues during anastomosis procedures, which can both reduce the risks during the surgical procedure and also provide a significant reduction in the amount of time required to perform certain anastomosis procedures. These anastomosis devices include a balloon that is inflated in the patient's bladder to keep the device in place during the healing process.

The tissue approximating structures can be activated by a number of different actuation mechanisms that the surgeon can use to extend and retract the tissue approximating structures relative to adjacent tissue structures, as desired. These actuation mechanisms can advantageously be provided to control tissue approximating structures that can take the form of at least one relatively sharp elongate structure (e.g., a sharp-ended needle or tine) that can be extended from the elongated body of the device to contact and optionally penetrate into or through tissue for approximation. However, because the tissue approximation structures are often positioned adjacent to the balloon of the anastomosis device, there is a need to configure the anastomosis device so that the approximation structures do not unintentionally come into contact with and/or damage the balloon.

SUMMARY OF THE INVENTION

Anastomosis devices and related surgical tools and external connecting devices of the invention preferably include an elongated catheter body, tissue approximating structures that can extend and retract relative to the elongated body, and actuating mechanisms for extending and retracting the tissue approximating structures. Examples of such anastomosis devices are described, for example, in Applicants' co-pending U.S. patent application Ser. No. 10/646,383, filed Aug. 21, 2003, entitled "Anastomosis Device and Related Methods"; Ser. No. 10/919,545, filed Aug. 16, 2004, entitled "Anastomosis Device and Related Methods"; and Ser. No. 10/919,775 filed Aug. 16, 2004, entitled "Anastomosis Device and Related Methods", all of which are incorporated herein by reference in their entireties. The anastomosis devices also preferably include a drainage lumen that may extend as a channel through the length of the elongated body and that communicates at its distal end with a drainage aperture, and a balloon at or adjacent to the distal end of the device. The concepts of the invention include devices, configurations and positioning for tissue approximation structures that minimize or eliminate contact between the approximation structures and the balloon and/or any resulting damage to the balloon.

More specifically, the tissue approximating structures for the anastomosis devices of the invention can include two sets of approximating structures or tines spaced from each other along the length of the catheter body that can be extended and retracted from the catheter body. Each of the sets of tissue approximating structures may be sequentially deployable in such a way that the surgeon can activate a tissue approximation structure to engage a first tissue structure, verify that an adjacent second tissue structure is properly positioned relative to the first tissue structure, then activate a second tissue approximation structure to engage that adjacent second tissue structure. Each of the tissue approximation structures may be controlled by a single actuation mechanism that is attached to the anastomosis device and is positioned outside the patient's body. The actuating mechanisms for the tissue approximating structures are located generally near a proximal end of the device and are preferably connected to the tissue approximating structures with at least one actuation wire, tube, lumen, or other mechanism. A separate actuation mechanism is preferably provided for each set of tissue approximating structures to allow for independent extension and retraction of the tissue approximating structures, as desired. Alternatively multiple actuation mechanisms can be connected to each other to provide a single actuation mechanism that is manipulated to provide the desired movement of the tissue approximating structures.

In one aspect of the invention, a surgical tool is provided which comprises an elongated body having a proximal end and a distal end, first and second sets of tissue approximating structures having deployed and retracted positions relative to the elongated body, an actuating mechanism at the proximal end of the elongated body for independently deploying and retracting each of the first and second sets of tissue approximating structures that have different configurations and a drainage lumen extending from a drainage aperture at the distal end of the elongated body to the proximal end. The surgical tool further includes a main balloon adjacent to the distal end of the elongated body.

In one embodiment, distal ends of at least one of the tines of the first set of tissue approximating structures is more sharp than at least one of the distal ends of the tines of the second set of tissue approximating structures, and the second set of tissue approximating structures can be closer than the first set of tissue approximating structures to the main balloon of the elongated body. The second set of tissue approximating structures may further include an enlarged portion at the distal end of at least one of its elongated tines, such as a ball, a flap, or an elliptical portion. In another embodiment, at least one of the first and second sets of tissue approximating structures comprises at least one preshaped tine structure, wherein the set of tissue approximating structures comprising the at least one preshaped tine structure may be positioned closer than the other set of tissue approximating structures to the main balloon. Each preshaped tine structure may be made of a material having a memory that allows it to be in a deformed configuration when retracted and to be in a preshaped configuration when deployed.

In another aspect of the invention, a surgical tool is provided that comprises an elongated body having a proximal end, a distal end, and at least one aperture extending through at least a portion of the body, first and second sets of tissue approximating structures having deployed and retracted positions relative to the elongated body, an actuating mechanism at the proximal end of the elongated body for independently deploying and retracting each of the first and second sets of tissue approximating structures, and a drainage lumen extending from a drainage aperture at the distal end of the elongated body to the proximal end. The tool further includes a main balloon adjacent to the distal end of the elongated body, and a second balloon spaced from the main balloon toward the proximal end of the elongated body, wherein the second balloon has an expanded condition in which it diverts one of the first and second tissue approximating structures from contacting the main balloon.

The main balloon and the second balloon may be independently expandable. In addition, the second balloon can be positioned adjacent to the base of at least one tine of a set of tissue approximating structures such that expansion of the second balloon moves a portion of each of the tines radially away from the elongated body.

In yet another aspect of the invention, a surgical tool is provided that comprises an elongated body having a proximal end and a distal end, first and second tissue approximating structures having deployed and retracted positions relative to the elongated body, an actuating mechanism at the proximal end of the elongated body for independently deploying and retracting each of the first and second sets of tissue approximating structures, a drainage lumen extending from a drainage aperture at the distal end of the elongated body to the proximal end, and a main balloon adjacent to the distal end of the elongated body. The first tissue approximating structure comprises a flexible material at least partially surrounding the elongated body and extending along a portion of a length of the elongated body. The material of the first tissue approximating structure can be slideable along the length of the elongated body and may comprise a mesh material.

BRIEF DESCRIPTION OF THE DRAWINGS

The invention will be further explained with reference to the appended Figures, wherein like structure is referred to by like numerals throughout the several views, and wherein:

FIG. 7 is a perspective view of a portion of an anastomosis device including another embodiment of tissue approximating structures of the invention;

FIG. 8 is a front view of the tissue approximating structure of FIG. 7 in its retracted condition;

FIG. 9 is a front view of the tissue approximating structure of FIGS. 7 and 8, with the tissue approximating structure in its deployed condition;

FIG. 11 is a front view of a portion of an anastomosis device having an extendible tissue approximating structure shown in its undeployed condition;

FIG. 12 is a front view of the portion of the anastomosis device of FIG. 11, with the extendible tissue approximating structure shown in its deployed condition;

DETAILED DESCRIPTION

Figure 1:
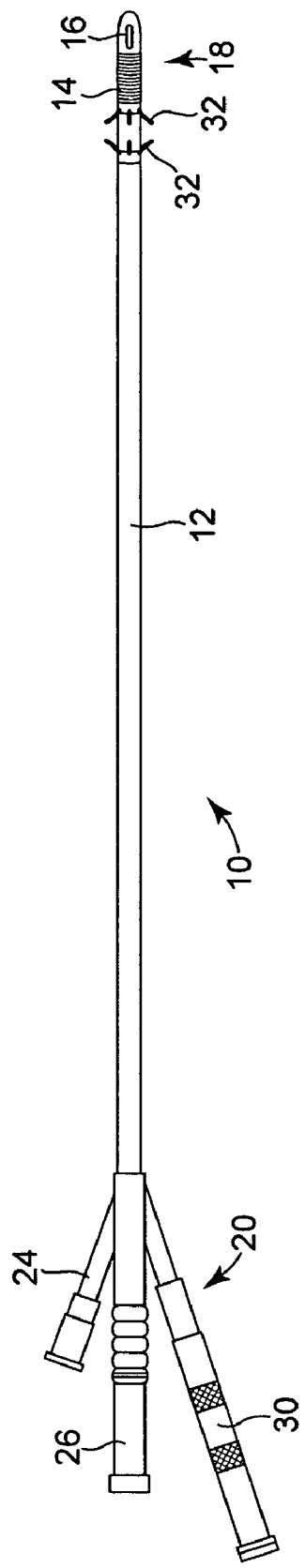
FIG. 1 is a top view of an exemplary anastomosis device of the type that can be used with the various configurations of the invention.

Referring now to the Figures, wherein the components are labeled with like numerals throughout the several Figures, and initially to FIG. 1, an exemplary embodiment is shown of a modified-Foley-catheter-type anastomosis device of the type that can be used with the various configurations of the invention. Device 10 includes distal end 18, catheter body 12, balloon 14, and drainage aperture 16. Tissue approximating structure can extend from catheter body 12, for example, along catheter body 12 adjacent to the balloon 14 near distal end 18. Tissue approximating structure of device 10 is shown as two sets of tines 32 (shown in an at least partially deployed condition) but may alternatively include other structure or structures that may be used to place or hold severed tissue in contact with another opposing severed tissue for healing, as will be described herein relative to certain aspects of the invention.

Device 10 further includes proximal end 20 opposite distal end 18. In the illustrated embodiment, proximal end 20 includes a port 24 that may connect to a lumen (not shown) such as an inflation lumen for balloon 14 or a drainage lumen from aperture 16. Another port 26 can also be used with an inflation lumen or a drainage lumen. Device 10 further includes an actuating mechanism 30 for extending and retracting tines 32. The actuating mechanism can comprise, for example, a turnable knob or a lever that can be moved or rotated to extend or retract the tissue approximating structure or tines 32. Other variations of these features of the illustrated proximal end will be understood by those of skill or are described herein relative to features of the invention, and/or may be used in combination with the features of the invention. In accordance with the invention, variations of several elements of an anastomosis device of the type generally described above relative to FIG. 1 are described as follows relative to the remaining Figures. However, it is understood that the features, configurations, and methods described below may be used with devices having a different configuration than that described relative to FIG. 1.

FIGS. 2-15 illustrate a variety of different configurations for the tines or tissue approximating structures of an anastomosis device. Any of these configurations may be used alone or in conjunction with other configurations of tines or tissue approximating structures within a single anastomosis device. In particular, these configurations can be used to minimize the likelihood of unintentional interaction between the tissue approximating structures and the balloon. This can be accomplished, for example, by providing more blunt surfaces that will be less likely to damage the balloon if they come in contact with the balloon (i.e., the surfaces minimize the possibility of undesired interaction with the balloon). However, the tissue approximating structures of the invention desirably should maintain the approximation function of the device at the bladder interface and/or protect the balloon from damage.

In addition, FIGS. 2-15 generally illustrate exemplary embodiments of end portions of an anastomosis device in conjunction with various tissue approximating structure configurations. These end portions are located generally at the distal end of an anastomosis device of the type described above. Alternatively, the exemplary end portions and corresponding tissue approximating structure of the invention may be used in a different type of device to perform anastomosis or other surgical techniques that require deployment of structures such as tines or tissue approximating structure, for example. Each of these end portions generally embodies the tip area of the device that is inserted into a patient and is located at the opposite end of the anastomosis device from the portion of the device that will remain outside the patient. Further, any device with which the tissue approximating structure of the invention is used may include an actuation mechanism, device, and/or structure that is used to manipulate the tissue approximating structures when those structures are surgically positioned within a patient's body. The type of actuation mechanism used can vary depending on the input needed from the tissue approximating structure (e.g., linear or rotational movement, pressure, air, water, or the like).

Figure 2:
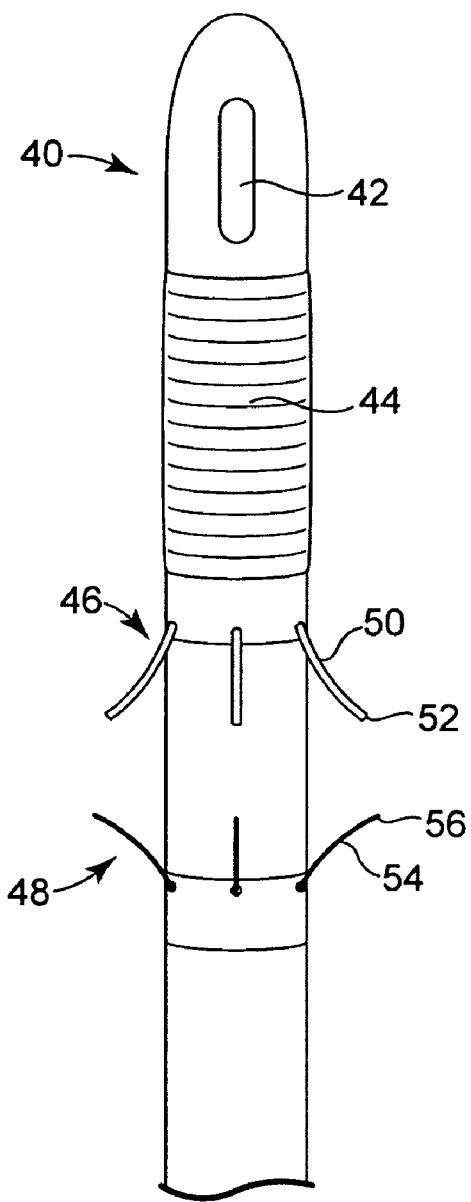
FIG. 2 is a front view of a portion of an anastomosis device including one embodiment of tissue approximating structures of the invention.

Referring to the embodiment of FIG. 2, an exemplary end portion 40 is shown that is located generally at the distal end of an anastomosis device of the type described above. End portion 40 includes a drainage aperture 42, a balloon or expanding portion 44, distal tissue approximating structure 46, and proximal tissue approximating structure 48. Distal tissue approximating structure 46 comprises a set of relatively flat and elongated tines or ribbons 50 having relatively blunt distal ends 52, while proximal tissue approximating structure 48 comprises a set of relatively narrow tines or wires 54 having ends 56 that are relatively sharp in comparison to ends 52 of tines or ribbons 50. For example, tines 54 may have a thin wire construction with sharp ends that resemble a flexible needle or pin.

In order to provide the functionality of two sets of tissue approximating structure along with added protection for balloon 44, balloon 44 is located closer to distal tissue approximating structure 46 having the tines or ribbons 50 with blunt ends 52 than to the tines 54 having sharper ends 56 (i.e., of proximal tissue approximating structure 48). That is, the sharper set of tines 54 are spaced further from balloon 44 to minimize the chances for its relatively sharper ends 56 to come in contact with and possibly damage balloon 44 when it is inflated or expanded. However, it is possible that the tissue approximating structure configurations are reversed such that the sharper set of tines is closer to balloon 44, if desired, such as for a particular surgical procedure. It is further possible that both the distal and proximal tissue approximating structures comprise relatively flat and elongated tines with blunt ends, such as the type illustrated as tines or ribbons 50. In any case, any tines that are provided with blunt ends are preferably sharp enough to be able to penetrate or otherwise reconnect severed tissues in a patient, but are preferably dull or blunt enough to decrease the risk of puncturing the balloon or otherwise damaging components and/or the patient.

It is noted that the tines described above and/or any of the other tissue approximation structures or tines described herein may be made of a material such as nitinol, metal, plastic, or any other material that is capable of being used in the human body (i.e., biocompatible) and that provides both the desired strength and flexibility to the device. Further, the length of any tissue approximating structure shown in the figures is only intended to be representative and the actual lengths selected will depend upon the particular surgical techniques to be performed, the material from which the tissue approximating structure is manufactured, and other preferences or requirements for the tissue approximation procedure. In addition, it is possible that all of the tines or extensions from a particular tissue approximating structure are not identical to each other and that at least some of the tines within a group of tines that make up a certain tissue approximating structure are different from other tines within that group. For example, a distal tissue approximating structure on a single anastomosis device may include tines with sharp ends and tines with blunt ends and/or may include a number of other features of tissue approximating structures that are described herein or otherwise known relative to tissue approximating structure configurations and options. In addition, the number of extensions, such as tines, that extend from the catheter body can be selected to include as few as one extension, or may have as many extensions as desired to provide the desired performance of the tissue approximation structures. Thus, while the description herein typically illustrates between approximately two and five extensions for a particular tissue approximating structure, it is understood that the number of extensions can vary widely from this number, depending on requirements of the surgical procedure to be performed.

Figure 3:
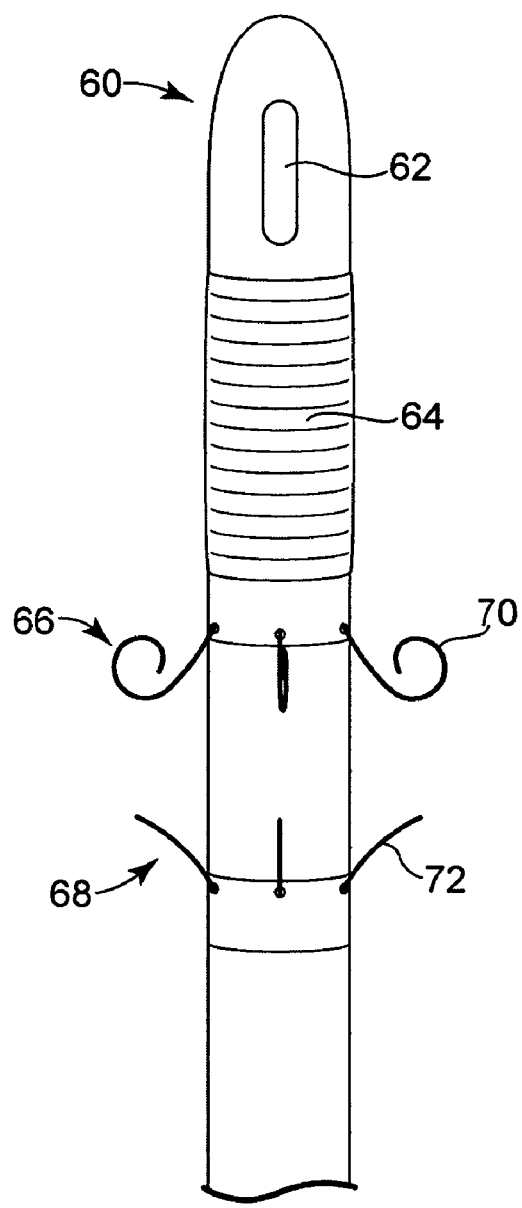
FIG. 3 is a front view of a portion of an anastomosis device including pre-shaped tissue approximating structures.

FIG. 3 illustrates another embodiment of an end portion 60 that is located generally at the distal end of an anastomosis device of the type described above. End portion 60 includes a drainage aperture 62, a balloon or expanding portion 64, distal tissue approximating structure 66, and proximal tissue approximating structure 68. Distal tissue approximating structure 66 comprises a set of tines 70 that are pre-shaped or molded to have a memory that allows them to curl back on themselves when not confined or otherwise straightened, preferably in a direction that prevents or limits them from contacting the balloon at any point before, during, or after the tissue approximation procedure occurs. That is, the tines 70 preferably are capable of being at least slightly deformed to accomplish a reconnecting of tissue and/or other processes, but the memory feature of the material preferably directs the ends of tines 70 away from balloon 64 when they are not otherwise being deformed or manipulated. Thus, the shapes of tines 70 can be selected and designed so that they can penetrate or otherwise reconnect severed tissue in a patient, but are otherwise positioned so that its ends are at a low risk of puncturing the balloon or otherwise damaging components and/or the patient.

Proximal tissue approximating structure 68 comprises a set of tines 72 that are relatively straight wire portions that may or may not be curved. The tines 70 and the tines 72 may be made of the same or different materials. In order to provide the functionality of two sets of tissue approximating structure along with added protection for balloon 64, balloon 64 is located closer to distal tissue approximating structure 66 having shaped tines 70 than to proximal tissue approximating structure 68 having tines 72. That is, the tines 72 are spaced further from balloon 64 than tines 70 that are designed with ends that curl away from balloon 64. However, it is possible that the tissue approximating structure configurations are reversed such that the straight set of tines is closer to balloon 64, if desired, such as for a particular surgical procedure. It is further possible that both the distal and proximal tissue approximating structures 66, 68 comprise curved tines.

Figure 4:
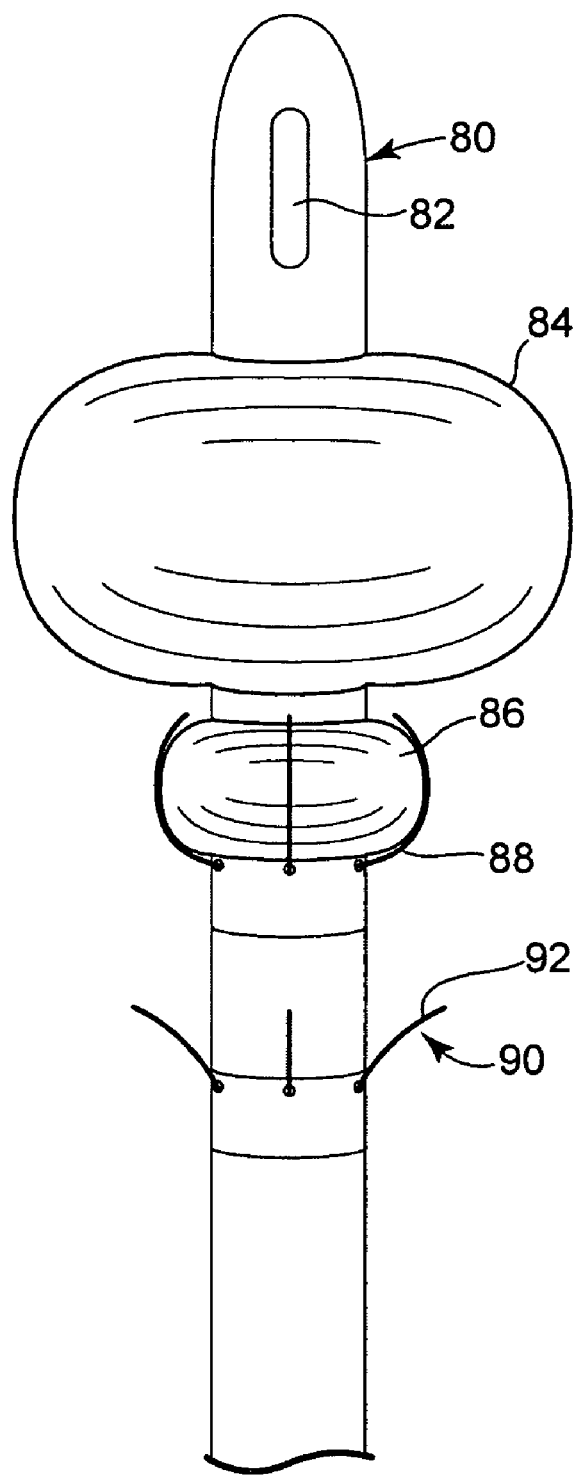
FIG. 4 is a front view of a portion of an anastomosis device including a secondary inflatable portion.

FIG. 4 illustrates another exemplary embodiment of an end portion 80 that is located generally at the distal end of an anastomosis device of the type described above. End portion 80 includes a drainage aperture 82, a primary balloon or expanding portion 84 (which is shown in an at least partially inflated or expanded condition in this figure), a secondary or auxiliary balloon 86 (which is also shown as being at least partially expanded or inflated in this figure), distal tissue approximating structure in the form of tines 88, and proximal tissue approximating structure 90. Secondary or auxiliary balloon 86 is provided to help prevent or minimize the possibility of tines 88 contacting or bending back against primary balloon 84 and thereby damaging balloon 84. Thus, secondary balloon 86 is preferably able to be inflated or expanded a sufficient amount to keep tines 88 from contacting balloon 84. The amount of inflation of secondary balloon 86 can vary considerably depending on the chosen shape, size, and material of tines 88. In devices where relatively large or long tines 88 are used, balloon 86 should be capable of being expanded to a larger size than the size that may be appropriate if relatively small or short tines are used. Further, the distance that balloon 86 is spaced from balloon 84 should also be selected so that inflation of balloon 86 does not interfere with balloon 84 or the tissue reconnection process.

Balloon 84 and balloon 86 may be made of the same or different materials and may be capable of being expanded or inflated to the same or a different size from each other. Balloon 84 and balloon 86 may be connected to the same or different sources for inflation or expansion, which may be located at the proximal end of the anastomosis device. In either case, it is possible that balloons 84, 86 can be inflatable independently from each other or that the inflation of one balloon 84, 86 causes some proportional inflation of the other balloon 84, 86. Further, secondary balloon 86 is preferably positioned close enough to the base of tines 88 that inflation of balloon 86 will cause the free portion of tines 88 to move outward relative to their bases in a relatively uniform manner without puncturing balloon 86. Balloon 86 may be provided with some type of limitation on its expansion so that it cannot expand to a size that allows it to interfere with the process of reconnecting severed tissues in a patient, which may be accomplished by using a material that is only expandable by a predetermined amount. Proximal tissue approximating structure 90 comprises a set of tines 92 that are shown as relatively straight, needle-like structures. The tines 88 and the tines 92 may be made of the same or different materials and may or may not be configured similarly to each other.

Balloon 84 is located closer to secondary balloon 86 and tines 88 than to tines 92 of tissue approximating structure 90. That is, the tines 92 are spaced further from balloon 84 than the tines 88 that are moveable by secondary balloon 86. However, it is possible that the tissue approximating structure configurations are reversed such that tines 92 are closer to balloon 84, if desired, such as for a particular surgical procedure. It is further possible that more than one secondary balloon 86 can be provided on a particular anastomosis device to divert or redirect a set of tines or other structures.

Figure 5:
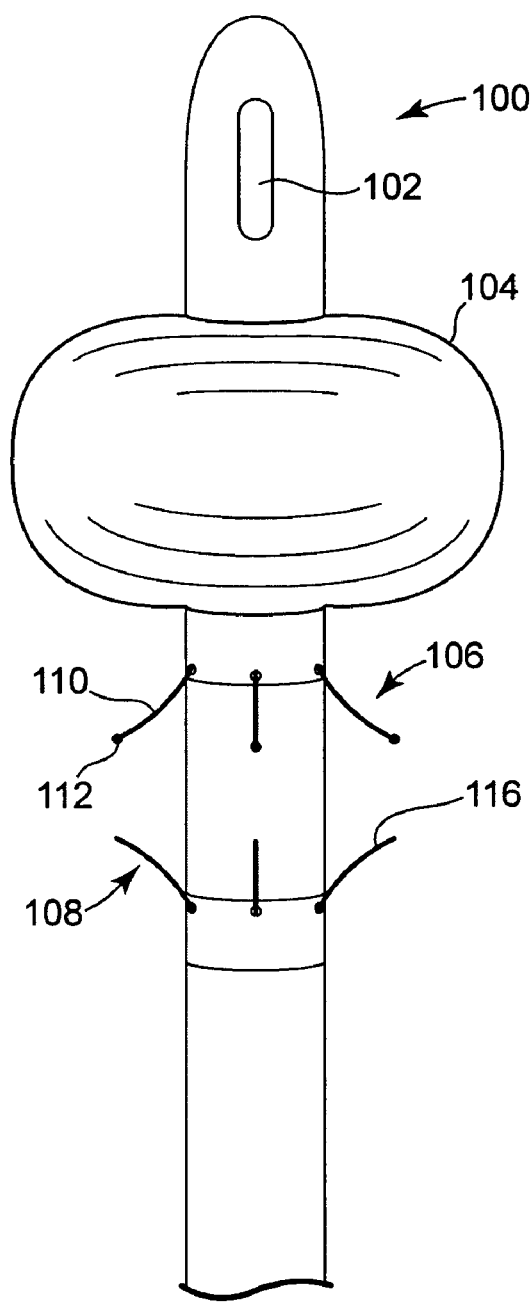
FIG. 5 is a front view of a portion of an anastomosis device including tissue approximating structures having enlarged tips.
Figure 6:
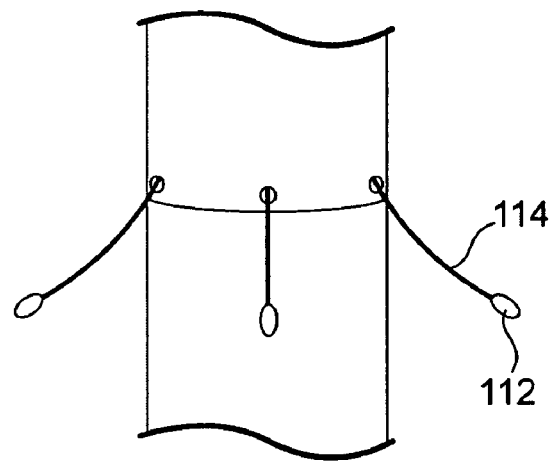
FIG. 6 is an enlarged front view of a portion of the device of FIG. 5.

FIGS. 5 and 6 illustrate another embodiment of an end portion 100 that is located generally at the distal end of an anastomosis device of the type described above, where FIG. 6 is an enlarged view of tissue approximating structure 106. End portion 100 of this embodiment includes a drainage aperture 102, a balloon or expanding portion 104, distal tissue approximating structure 106, and proximal tissue approximating structure 108. Distal tissue approximating structure 106 comprises a set of tines 110 that each include a wire or elongated portion 114 having an enlarged portion 112 at one end in the form of a ball, flap, or other shape. Enlarged portions 112 are provided to protect the balloon 104 from being damaged by sharp tine ends. These enlarged portions 112 may be preformed with their respective wire portion 114 and/or may be welded, adhered, or otherwise secured to the wire 114. Each enlarged portion 112 may be considerably larger than the cross-sectional area of the wire 114 from which it extends, or may be only slightly larger. Further, enlarged portions 112 may have any desired shape that will provide the function of protecting balloon 104, such as the cylindrical or elliptical shapes shown in the figures, or other desired shapes that are at least slightly less sharp than the needle-like tine ends that might otherwise be provided.

Proximal tissue approximating structure 108 comprises a set of relatively narrow tines 116, which may have a wire-like configuration with sharp ends. In order to provide the functionality of two sets of tissue approximating structure along with added protection for balloon 104, balloon 104 is located closer to distal tissue approximating structure 106 having tines 110 with enlarged portions 112 than to tines 116. However, it is possible that the tissue approximating structure configurations are reversed such that the sharper set of tines is closer to the balloon 104, if desired, such as for a particular surgical procedure. It is further possible that both the distal and proximal tissue approximating structures comprise at least one elongated wire portion having an enlarged end portion.

FIGS. 7-9 illustrate another configuration of a tissue approximating structure of the invention, including at least one set of extending structures that are relatively flexible, yet are strong enough to serve their functional purpose of maintaining approximation of tissues. In particular, FIG. 7 illustrates an end portion 120 of an anastomosis device that generally includes a drainage aperture 122, a balloon or expanding portion 124, distal tissue approximating structure 126, and proximal tissue approximating structure 128. Distal tissue approximating structure 126 comprises at least one flexible extension 130, each of which extends through a corresponding slot or opening 132 in catheter body 134. Extensions 130 are retractable and extendible relative to the openings 132, as desired for use in reconnecting tissues. In this embodiment, distal tissue approximating structure 126 includes multiple (e.g., four) extensions 130 attached at their proximal and distal ends to a moveable disk 136, as shown best in FIG. 8 (illustrating a retracted condition of extensions 130) and FIG. 9 (illustrating a deployed or extended condition of extensions 130). This structure 126 is positioned within the interior portion of catheter body 134 when the anastomosis device is assembled. For clarity of the illustration, any other structures that will be positioned within catheter body 134 are not illustrated in FIG. 7, although an operating device would include additional lumens and the like within catheter body 134.

In its retracted condition shown in FIG. 8, tissue approximating structure 126 includes disks 136 that are spaced far enough from each other that extensions 130 is generally straight. The outer surface of disks 136 are preferably sized to fit closely within the open center area of catheter body 134 so that the entire tissue approximating structure 126 can be contained within the walls of catheter body 134. When it is desired to deploy extensions 130 through corresponding slots or openings 132, an actuation mechanism is used to force moveable disks 136 closer to each other by moving either one or both of the disks 136 toward the other of the disks 136. In this way, extensions 130 will be deformed to bulge or extend outwardly from a centerline 137, as shown. In certain preferred orientations of tissue approximating structure 126 within catheter body 134, extensions 130 will be aligned so that they extend through slots or openings 132 when deployed. In fact, openings 132 may dictate where extensions 130 can form in that the extensions 130 will press on the inside of catheter body 134 until enough internal pressure causes extensions 130 to move out through openings 132. The bent or curved end of extensions 130 provide blunt ends that are preferably sharp enough to be able to penetrate or otherwise reconnect severed tissues in a patient, but that are dull or blunt enough to minimize the risk of puncturing the balloon or otherwise damaging components and/or the patient. It is possible, however, that extensions are relatively sharp once configured in the manner shown in FIGS. 7 and 9.

Proximal tissue approximating structure 128 comprises a set of tines 129 that are generally narrow tines that have a structure that is similar to a wire. In order to provide the functionality of two sets of tissue approximating structure along with added protection for balloon 124, balloon 124 is located closer to distal tissue approximating structure 126 having flexible extensions 130 than to the tines 129. That is, tines 129 are spaced further from balloon 124 to minimize the chances for its ends to come in contact with and possibly damage the balloon 124 when it is inflated or expanded. However, it is possible that the tissue approximating structure configurations are reversed such that tines 129 are closer to balloon 124, if desired, such as for a particular surgical procedure. It is further possible that both the distal and proximal tissue approximating structures are configured the same as the tissue approximating structure 126.

Figure 10:
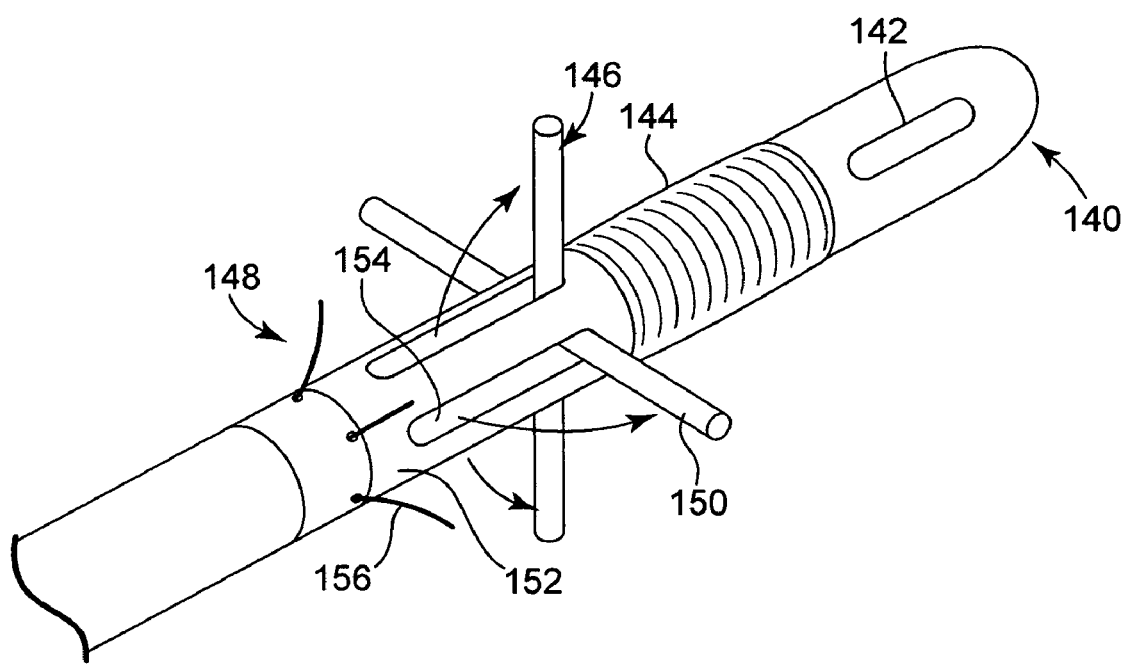
FIG. 10 is a perspective view of a portion of an anastomosis device including one embodiment of tissue approximating structures that pivot relative to the body of the device.

FIG. 10 shows an end portion 140 of another exemplary anastomosis device that is similar to the embodiment illustrated in FIG. 7. That is, end portion 140 generally includes a drainage aperture 142, a balloon or expanding portion 144, distal tissue approximating structure 146, and proximal tissue approximating structure 148. End portion 140 further includes a catheter body 152 having at least one slot or recessed area 154, which may be similar in configuration to the slots 132 of end portion 120 of FIG. 7. In the embodiment of FIG. 10, distal tissue approximating structure 146 comprises at least one extension or paddle 150, the number of which preferably corresponds with the number of slots or recessed areas 154. Extensions 150 are retractable and extendible toward and away from slots 154, respectively, as desired for use in reconnecting tissues. In particular, extensions 150 are able to pivot about one end to allow for retraction and extension thereof relative to catheter body 152. Extensions 150 are provided with relatively blunt ends that are preferably able to penetrate, support, or otherwise reconnect severed tissues in a patient, but are preferably dull or blunt enough to decrease the risk of puncturing the balloon or otherwise damaging components and/or the patient.

Proximal tissue approximating structure 148 comprises a set of tines 156 that are generally narrow or thin tines that have a structure that is similar to a wire. In order to minimize the chances for tissue approximating structure to come in contact with and possibly damage balloon 144 when it is inflated or expanded, tines 156 are spaced to be further from balloon 144 than the distance between balloon 144 and distal tissue approximating structure 148 having retractable extensions 150. However, it is possible that the tissue approximating structure configurations are reversed such that tines 156 are closer to the balloon 144, if desired, such as for a particular surgical procedure. It is further possible that both the distal and proximal tissue approximating structures are configured the same as the tissue approximating structure 146.

FIGS. 11 and 12 illustrate another embodiment of an end portion 160 that is located generally at the distal end of an anastomosis device of the type described above. End portion 160 of this embodiment includes a catheter body 170 having a drainage aperture 162, a balloon or expanding portion 164, a braided structure 166, and proximal tissue approximating structure 168. Braided structure 166 includes an elongated mesh or braided material that surrounds a portion of catheter body 170 between balloon 164 and proximal tissue approximating structure 168. Braided structure 166 extends along at least a portion of the length of catheter body 170 between balloon 164 and proximal tissue approximating structure 168. In its undeployed or retracted condition, shown in FIG. 11, a top edge 172 of structure 166 is positioned adjacent to balloon 164 and a bottom edge 174 of structure 166 spaced from top edge 172 and is positioned to optionally cover proximal tissue approximating structure 168. As shown in FIG. 11, structure 166 in its undeployed condition is generally cylindrical in shape to closely match the outer surface of catheter body 170. In its deployed or extended condition, shown in FIG. 12, bottom edge 174 has been moved upwardly toward top edge 172 so that structure 166 bulges outwardly to form a disk-like structure extending from catheter body 170. In this position, proximal tissue approximating structure 168, which consists of at least one tine 176, is exposed such that any tine or tines 176 or other structures are available for reconnecting tissue.

To form this disk-like configuration, either one or both of the top edge 172 and bottom edge 174 can be moved toward the other of the edges in order to achieve the desired position of the structure 166. However, it is contemplated that one of the edges 172, 174 can be fixed or secured to catheter body 170, with the other of the edges 172,174 being moveable along the length of catheter body 170.

In any case, structure 166 will bulge or extend outwardly by an amount that is proportional to or otherwise corresponds with the distance between edges 172, 174, which is controlled by an actuation mechanism. That is, the disk-like configuration of structure 166 will extend further from catheter body 170 as the edges 172, 174 are moved closer to each other, which provides a manner of controlling a desired amount of extension of the structure 166. When structure 166 is deployed, as in FIG. 12, the extended portion provides protection for balloon 164 from being damaged by sharp tine ends, such as from proximal tissue approximating structure 168. Further, it is contemplated that structure 166 is made of a material that is not braided or mesh-like, but is a more solid thin material, such as a tightly woven fabric or relatively thin plastic film, for example. However, it is desirable that the material or materials used for structure 166 have enough structural integrity to be able to be formed into and maintain the extended ring configuration shown in FIG. 12.

Figure 13:
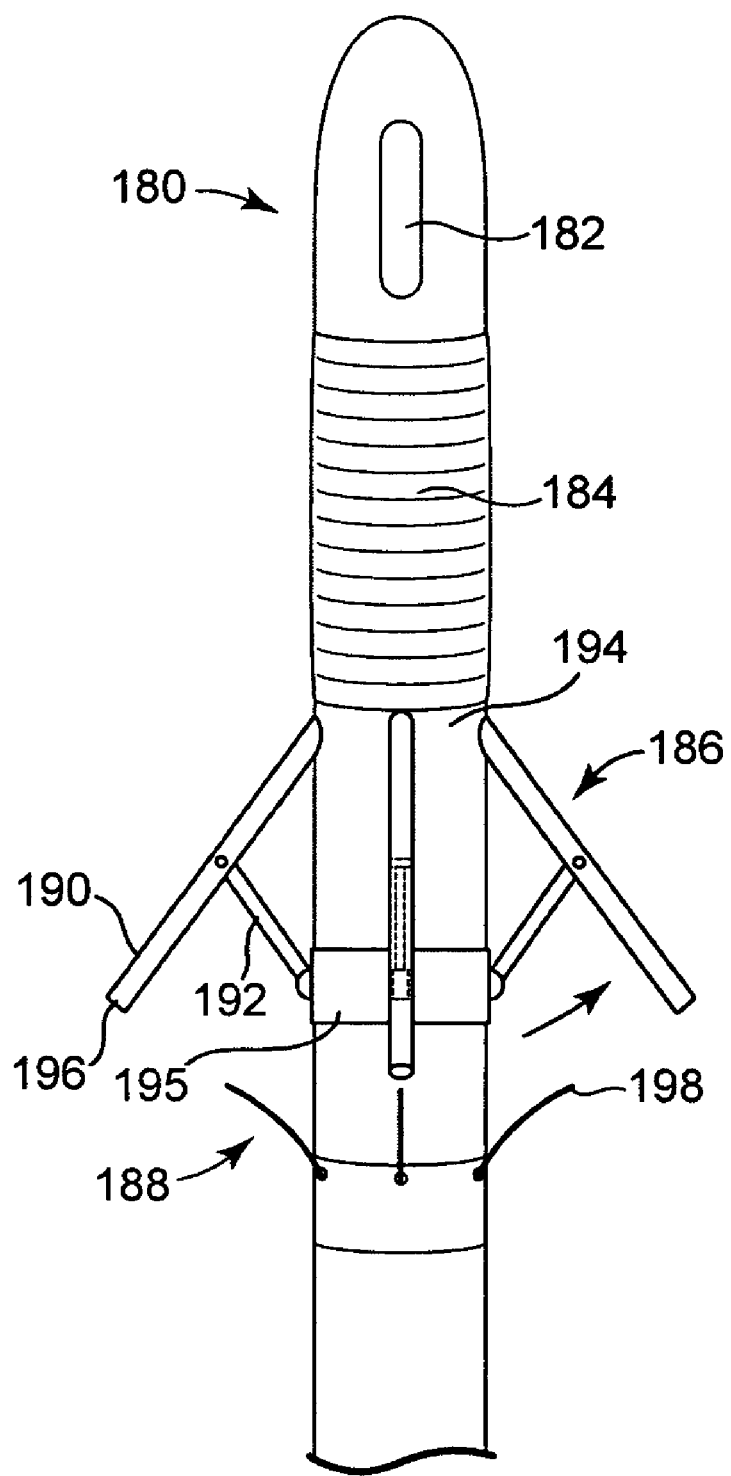
FIG. 13 is a front view of a portion of an anastomosis device including a hinged embodiment of tissue approximating structures.

FIG. 13 illustrates another embodiment of an end portion 180 that is located generally at the distal end of an anastomosis device. End portion 180 of this embodiment includes a drainage aperture 182, a balloon or expanding portion 184, distal tissue approximating structure 186, and proximal tissue approximating structure 188. Distal tissue approximating structure 186 includes at least one flap 190 that is connected at one end to a catheter body 194, and is connected to a connector portion 192 at a point between its two ends. Each connector portion 192 is connected to a slideable collar 195 at one end and to flap 190 at its other end. Collar 195 can be moved or slid along the length of catheter body 194 to cause both flap 190 and connector portion 192 to pivot relative to each other and relative to catheter body 194. This movement of the hinged structure can retract flap 190 toward catheter body 194 and deploy or extend flap 190 away from catheter body 194, as desired. Slots or openings may also be provided in catheter body 194 to at least partially contain flaps 190 when in their retracted configuration.

Flaps 190 each have a free end 196 that can have a configuration that will provide the function of protecting balloon 184 from being damaged, although it is possible that ends 196 are relatively sharp. Proximal tissue approximating structure 188 comprises a set of relatively narrow or wire-like tines 198. In order to provide the functionality of two sets of tissue approximating structure along with added protection for balloon 184, balloon 184 is located closer to distal tissue approximating structure 186 than to tines 198. However, it is possible that the tissue approximating structure configurations are reversed such that the sharper set of tines is closer to the balloon 184, if desired, such as for a particular surgical procedure. It is further possible that both the distal and proximal tissue approximating structures comprise hinged structures.

Figure 14:
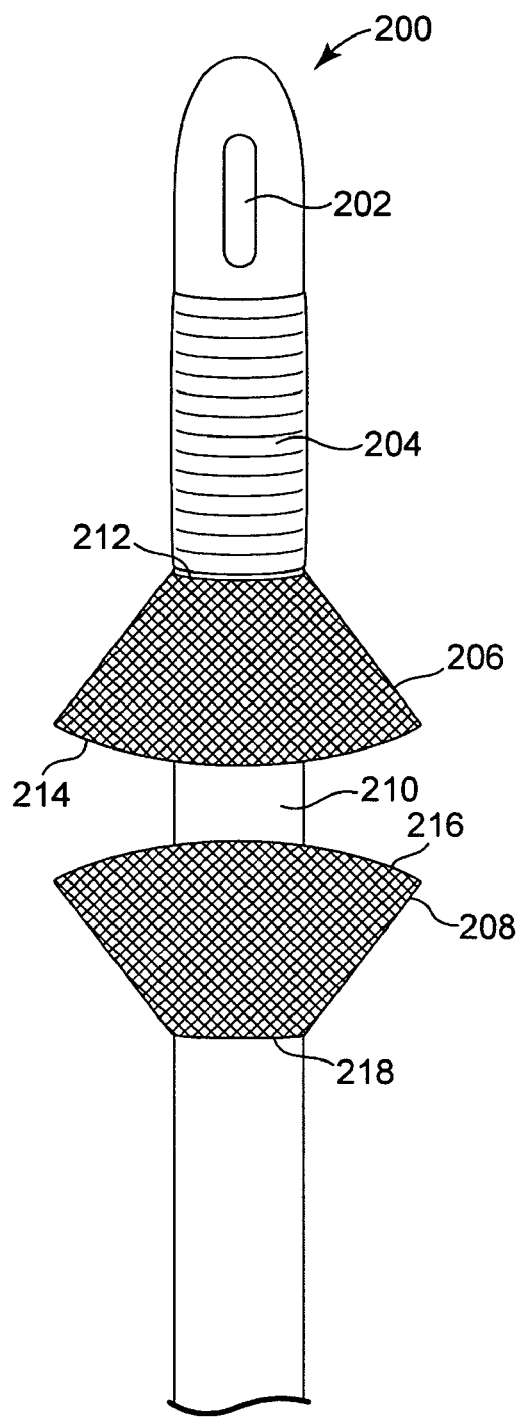
FIG. 14 is a front view of a portion of an anastomosis device having extendible tissue approximating structure shown in its deployed condition.
Figure 15:
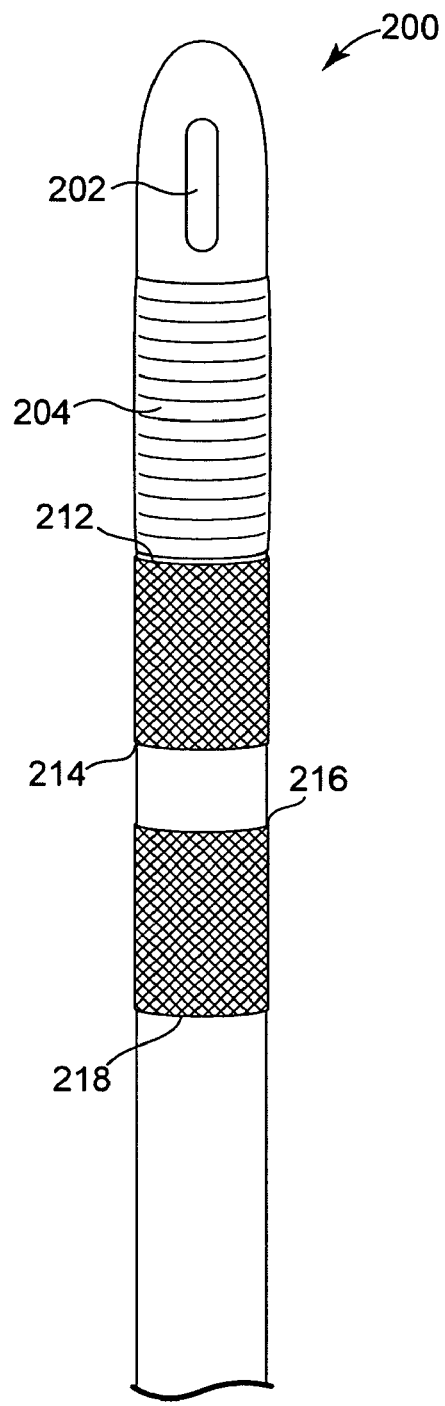
FIG. 15 is a front view of the portion of the anastomosis device of FIG. 14, with the extendible tissue approximating structure shown in its retracted or undeployed condition.

FIGS. 14 and 15 illustrate another embodiment of an end portion 200 that is located generally at the distal end of an anastomosis device. End portion 200 of this embodiment includes a drainage aperture 202, a balloon or expanding portion 204, distal tissue approximating structure 206, and proximal tissue approximating structure 208. Distal tissue approximating structure 206 includes a first end 212 adjacent to balloon 204 and a second end 214 spaced further from balloon 204. In its undeployed or retracted condition, shown in FIG. 15, distal tissue approximating structure 206 is generally cylindrical in shape to closely match the outer surface of a catheter body 210. In its deployed or extended condition, shown in FIG. 14, second end 214 of tissue approximating structure 206 is further from catheter body 210 than first end 212, such as may be provided by expanding tissue approximating structure 206 by inflation. That is, structure 206 may be provided as a bladder that is more free to expand at its second end 214 than its first end 212, thereby providing the tapered shape to the structure 206. Alternatively, distal tissue approximating structure 206 may include an outer mesh or braided material that can be moved outwardly at its second end 214 through the use of a bladder or some other structure that is positioned between the outer material and the catheter body.

As shown in FIGS. 14 and 15, proximal tissue approximating structure 208 is configured similarly to the distal tissue approximating structure 206, however, the structure 208 is oppositely oriented along the length of catheter body 210 so that an end 216, which is closer to balloon 204 than an end 218, is the end that can move outwardly relative to catheter body 210 in a type of flare, such as through the use of a bladder or some other structure that provides the tapered extension shown in FIG. 14. It is understood that proximal tissue approximating structure 208 is optional and that end portion 200 may instead be provided with only distal tissue approximating structure 206. In this case, another tissue approximating structure configuration can be used for tissue approximating structure 208.

The sequence of using anastomosis devices that include many of the tissue approximating structure variations described herein can be similar, although the mechanisms used to deploy the structures can be different. In general, tissue approximating structures can first be provided to a surgeon in their undeployed or retracted positions within the attached catheter body. When it is desired to deploy the tissue approximating structures, an actuation device or mechanism is activated to either sequentially or simultaneously deploy one or more tissue approximating structures. The actuation mechanisms may include a defined set of steps that are required for proper deployment of tissue approximating structures, or the actuation may be achieved by a single movement or step. The retraction of the tissue approximating structures can then be achieved by performing the opposite actions as were used for deployment of the structures. The tissue approximating structures can be deployed or retracted in a predefined sequence (e.g., bladder tines then urethral tines) as desired for the surgical procedure.

The various embodiments described herein are not necessarily limited to male-oriented or related surgical procedures and may be applied to either gender and possibly to animals.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention.

The invention claimed is:

1. A surgical tool comprising:
   an elongated body having a proximal end, a distal end, an outer cylindrical surface, and a longitudinal axis extending from the proximal end to the distal end;
   first and second sets of tissue approximating structures having a retracted position relative to the elongated body in which the tissue approximating structures of the first and second sets do not extend past the outer surface of the elongated body, and a deployed position relative to the elongated body in which at least one of the tissue approximating structures of each of the first and second sets extends from the outer surface of the elongated body at an angle relative to its longitudinal axis;

an actuating mechanism at the proximal end of the elongated body for independently deploying and retracting each of the first and second sets of tissue approximating structures;

a drainage lumen extending from a drainage aperture at the distal end of the elongated body to the proximal end; and a main balloon adjacent to the distal end of the elongated body;

wherein each of the first and second sets of tissue approximating structures includes at least one elongated tine having a distal end, and wherein the second set of tissue approximating structures comprises an enlarged shaped element at the distal end of at least one of its elongated tines.

2. The surgical tool of claim 1, wherein the distal ends of at least one of the tines of the first set of tissue approximating structures is more sharp than at least one of the distal ends of the tines of the second set of tissue approximating structures.

3. The surgical tool of claim 2, wherein the second set of tissue approximating structures is closer than the first set of tissue approximating structures to the main balloon of the elongated body.

4. The surgical tool of claim 1, wherein the enlarged shaped element is one of a ball, a flap, and an elliptical portion.

5. The surgical tool of claim 1, wherein at least one of the first and second sets of tissue approximating structures comprises at least one preshaped tine structure.

6. The surgical tool of claim 5, wherein the set of tissue approximating structures comprising the at least one preshaped tine structure is positioned closer to the main balloon than the other set of tissue approximating structures.

7. The surgical tool of claim 5, wherein each preshaped tine structure includes a distal end that is directed away from the main balloon.

8. The surgical tool of claim 5, wherein each preshaped tine structure is comprised of a material having a memory that causes the preshaped tine structure to be in a deformed configuration when retracted and to be in a preshaped configuration when deployed.

9. A surgical tool comprising:
an elongated body having a proximal end, a distal end, and at least one aperture extending through at least a portion of the body;
first and second sets of tissue approximating structures having deployed and retracted positions relative to the elongated body;
an actuating mechanism at the proximal end of the elongated body for independently deploying and retracting each of the first and second sets of tissue approximating structures;
a drainage lumen extending from a drainage aperture at the distal end of the elongated body to the proximal end;
a main balloon adjacent to the distal end of the elongated body; and
a second balloon spaced from the main balloon toward the proximal end of the elongated body, wherein the second balloon has an expanded condition in which it diverts one of the first and second tissue approximating structures away from the main balloon; wherein each of the first and second sets of tissue approximating structures includes at least one elongated tine having a distal end, and wherein the second set of tissue approximating structures comprises an enlarged shaped element at the distal end of at least one of its elongated tines.

10. The surgical tool of claim 9, wherein the main balloon and the second balloon are independently expandable.

11. The surgical tool of claim 9, wherein the second balloon is positioned adjacent to the base of the at least one tine of the second set of tissue approximating structures such that expansion of the second balloon moves a portion of each of the tines radially away from the elongated body.

12. The surgical tool of claim 1, wherein the second set of tissue approximating structures includes at least one extension that is pivotable toward and away from the elongated body.

13. The tool of claim 12, wherein the at least one pivotable extension of the second tissue approximating structure is hingedly connected to the elongated body.

14. A surgical tool comprising:
an elongated body having a proximal end and a distal end;
first and second tissue approximating structures having deployed and retracted positions relative to the elongated body;
an actuating mechanism at the proximal end of the elongated body for independently deploying and retracting each of the first and second sets of tissue approximating structures;
a drainage lumen extending from a drainage aperture at the distal end of the elongated body to the proximal end; and
a main balloon adjacent to the distal end of the elongated body;
wherein the first tissue approximating structure comprises a flexible material at least partially surrounding the elongated body and extending along a portion of a length of the elongated body; wherein each of the first and second sets of tissue approximating structures includes at least one elongated tine having a distal end, and wherein the second set of tissue approximating structures comprises an enlarged shaped element at the distal end of at least one of its elongated tines.

15. The surgical tool of claim 14, wherein the first tissue approximating structure comprises a material that is slideable along the length of the elongated body.

16. The surgical tool of claim 15, wherein the first tissue approximating structure has a first length when in a first position and a second length when in a second position, wherein the second length is shorter than the first length, and wherein the first tissue approximating structure extends further radially from the elongated body when in the second position than when in the first position.

17. The surgical tool of claim 15, wherein the first tissue approximating structure comprises a mesh material.

18. The surgical tool of claim 15, wherein the second tissue approximating structure comprises a plurality of tines.

19. The surgical tool of claim 16, wherein the second tissue approximating structure is at least partially covered by the first tissue approximating structure when the first tissue approximating structure is in the first position.

20. The surgical tool of claim 14, wherein the second tissue approximating structure comprises a flexible material at least partially surrounding the elongated body and extending along a portion of a length of the elongated body.

21. The surgical tool of claim 20, wherein at least one of the first and second tissue approximating structures has a fixed end secured to the elongated body and an opposite end that is radially moveable relative to the elongated body.

22. The surgical tool of claim 21, wherein both the first and second tissue approximating structures have a fixed end secured to the body and an opposite end that is radially moveable relative to the elongated body.

23. A surgical tool comprising:
   an elongated body having a proximal end, a distal end, and an outer surface;
   a main balloon adjacent to the distal end of the elongated body;
   a first set of tissue approximating structures spaced in a proximal direction from the main balloon and having deployed and retracted positions relative to the outer surface of the elongated body;
   a second set of tissue approximating structures spaced in a proximal direction from the first set of tissue approximating structures and having deployed and retracted positions relative to the outer surface of the elongated body;
   an actuating mechanism at the proximal end of the elongated body for independently deploying and retracting each of the first and second sets of tissue approximating structures relative to the outer surface of the elongated body; and
   a drainage lumen extending from a drainage aperture at the distal end of the elongated body to the proximal end;
   wherein the first set of tissue approximating structures has a different configuration than the second set of tissue approximating structures; wherein each of the first and second sets of tissue approximating structures includes at least one elongated tine having a distal end, and wherein the second set of tissue approximating structures comprises an enlarged shaped element at the distal end of at least one of its elongated tines.

* * * * *